United States Patent [19]

Wessels et al.

[11] Patent Number: 4,697,579

[45] Date of Patent: Oct. 6, 1987

[54] APPARATUS FOR ACOUSTIC IRRADIATION OF PATHOLOGICAL CHANGES IN A PATIENT

[75] Inventors: Gerd Wessels; Arnim Rohwedder, both of Erlangen, Fed. Rep. of Germany

[73] Assignee: Siemens Aktiengesellschaft, Berlin and Munich, Fed. Rep. of Germany

[21] Appl. No.: 890,116

[22] Filed: Jul. 28, 1986

[30] Foreign Application Priority Data

Aug. 19, 1985 [DE] Fed. Rep. of Germany ... 8523751[U]

[51] Int. Cl.[4] .............................................. A61B 17/22
[52] U.S. Cl. .................................. 128/24 A; 128/328
[58] Field of Search ..................... 128/328, 24 A, 660, 128/661, 662, 663, 804

[56] References Cited

U.S. PATENT DOCUMENTS

| 3,237,623 | 3/1966 | Gordon | 128/24 A |
| 3,942,531 | 3/1976 | Hoff et al. | 128/328 |
| 4,135,497 | 1/1979 | Meyers et al. | 128/736 |
| 4,355,643 | 10/1982 | Laughlin et al. | 128/663 |
| 4,530,358 | 7/1985 | Forssmann et al. | 128/328 |
| 4,620,545 | 11/1986 | Shene et al. | 128/24 A |

FOREIGN PATENT DOCUMENTS

| 0090138 | 10/1983 | European Pat. Off. |
| 0131654 | 1/1985 | European Pat. Off. |
| 2018468 | 10/1970 | Fed. Rep. of Germany |
| 2351247 | 10/1975 | Fed. Rep. of Germany |
| 2648908 | 5/1978 | Fed. Rep. of Germany |
| 2140693 | 12/1984 | United Kingdom |

Primary Examiner—Lee S. Cohen
Assistant Examiner—J. P. Lacyk
Attorney, Agent, or Firm—Hill, Van Santen, Steadman & Simpson

[57] ABSTRACT

The present invention is directed to a method and apparatus for acoustic irradiation of a pathological change in a patient comprising a housing containing a shock wave generator positioned in a fluid-filled focusing chamber closed by a membrane characterized by a ring of elastic material being secured to the housing and surrounding the membrane and projecting beyond the membrane while in an idle position. The ring is provided with a channel system to allow evacuation of air from the space between the ring, membrane and the skin of the patient and also for introducing a coupling fluid into this space. The housing includes a channel for introducing additional fluid into the fluid-filled focusing chamber to cause the membrane to be expanded into the space and to engage the skin of the patient with a thin film of the coupling fluid disposed therebetween.

3 Claims, 1 Drawing Figure

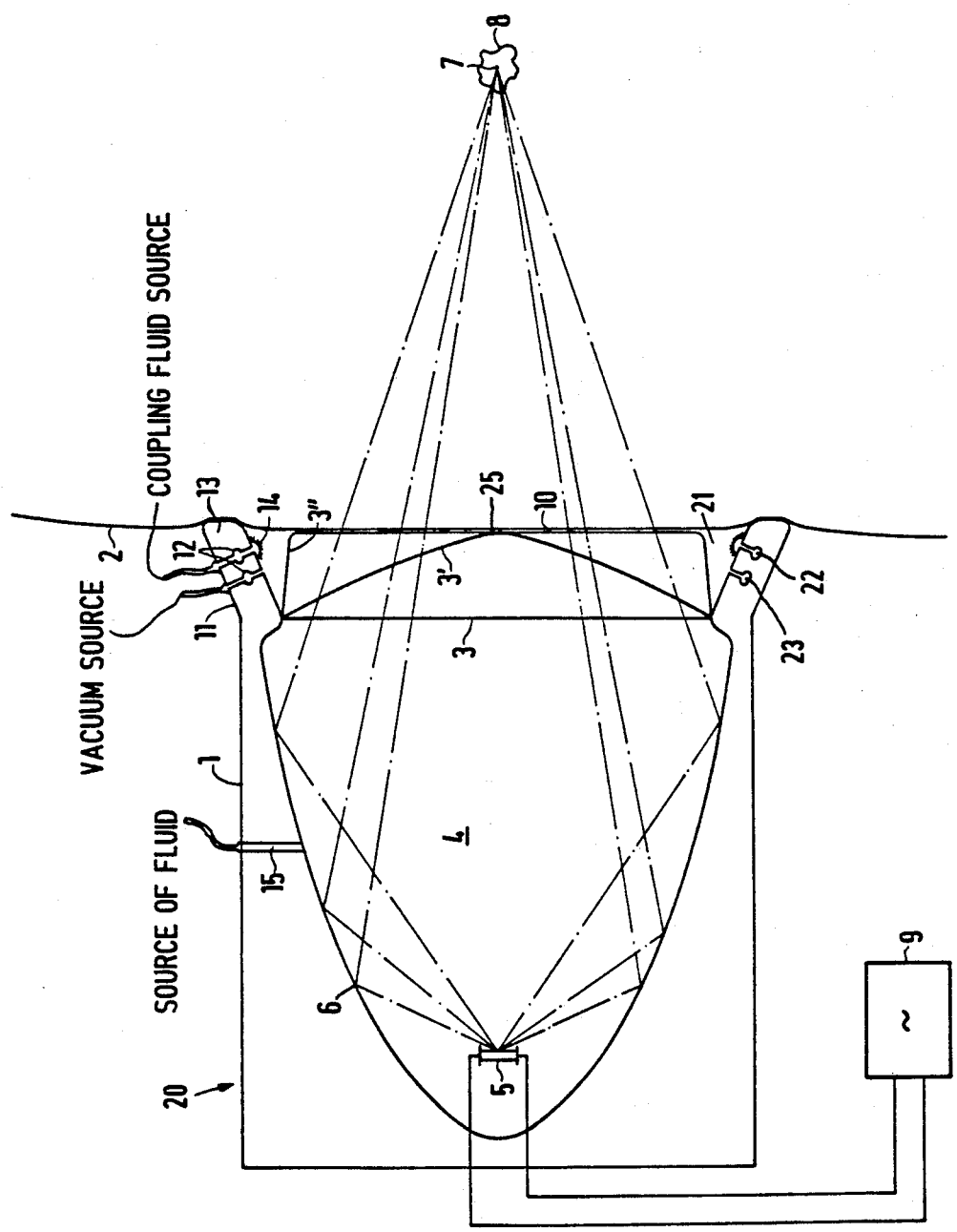

I'm 4,697,579

APPARATUS FOR ACOUSTIC IRRADIATION OF PATHOLOGICAL CHANGES IN A PATIENT

BACKGROUND OF THE INVENTION

The present invention is directed to an apparatus for an acoustic irradiation of a pathological change in a patient. The apparatus comprises a shock wave generator which will emit a shock wave through a liquid-filled space which is closed by a membrane.

An apparatus for breaking up concrements present in a body of a living being without contact is disclosed in U.S. Pat. No. 3,942,531 which was based on German Application No. 2,351,247 and whose disclosure is incorporated by reference thereto. This apparatus can be used for the disintegration of urinary calculi, renal calculi and gallstones. The apparatus operates with the assistance of a spark gap, which produces shock waves in the interior of a focusing chamber which is closed by an elastic membrane and the shock waves are transmitted to the membrane via a coupling fluid which is situated in the enclosed focusing chamber. The shape of the focusing chamber forms a part of an ellipse of revolution which has the shock wave generator disposed at one focal point. The shock waves generated by this generator are focused by the walls of the focusing chamber and are focused towards the other focal point of the ellipse of revolution, which other focal point lies outside of the chamber. For carrying out the disintegration of a calculi or stone, the following two conditions, among others, must be met:

(a) When the chamber is placed against the skin of the patient, the second focus point of the ellipse of revolution, which lies outside of the focusing chamber, must coincide with the position of the concrement; and (b) No air spaces should be situated between the membrane and the skin of the patient since this air space would prevent a good coupling of the waves due to their great difference in acoustical resistance. The presence of air spaces or gaps will increase the reflection of the acoustical waves.

SUMMARY OF THE INVENTION

The object of the present invention is to remove air spaces or pockets which are enclosed between a membrane of the focusing chamber when the apparatus of the present invention is initially applied to the patient.

This object is achieved by an improvement in an apparatus for acoustic irradiation of a pathological change in a patient, said apparatus comprising a housing forming a fluid-filled focusing chamber closed by a stretchable membrane, and having a shock wave generator positioned in the fluid-filled chamber to emit shock waves through the fluid-filled chamber. The improvements comprise a collar-like ring of elastic material being fastened to the housing and surrounding the stretchable membrane, said collar-like ring projecting beyond the membrane when the membrane is in an idle position and having a channel system for evacuating air out of the space between the ring, membrane and the patient's skin engaged by the ring and for introducing the coupling fluid into this space.

When the apparatus of the invention is applied to the body of the patient, the projecting collar-like rim will engage the patient's skin so that the membrane, while in an idle condition, will not yet come in contact with the skin. The ring, the membrane and the skin form a closed chamber or space which, however, is in communication with the channel system contained in the ring.

The air in the closed space or seating chamber, which is formed between the skin, the ring and the membrane, is first partially evacuated. The result of the under pressure or vacuum in the closed space or seating chamber causes air spaces or pockets enclosed on the surface of the skin, especially within the pores, to be greatly reduced. Subsequently, a coupling fluid can be injected into the chamber through specific channels of the channel system and this coupling fluid will cause a moistening of the skin surfaces, the inside walls of the ring and the outside surface of the elastic membrane. The seating chamber is further evacuated during the moistening so that the membrane arches out of its rest position as a consequence of the vacuum and engages the patient's skin beginning in the center of the membrane and preceding radially from this center point.

An inclusion of air, which is still present in this evacuation chamber, is thus, prevented by the membrane engaging the skin.

BRIEF DESCRIPTION OF THE DRAWINGS

FIG. 1 is a cross sectional view through the apparatus of the present invention illustrating the position of the membrane in an idle, and intermediate and final position as it is assembled onto the skin of a patient.

DESCRIPTION OF THE PREFERRED EMBODIMENTS

The principles of the present invention are particularly useful when incorporated in an apparatus generally indicated at 20, which is illustrated as being applied on a patient 2. The apparatus 20 has a housing 1 which surrounds a focusing chamber 4 which has a wall 6 which is an ellipse of revolution and is filled with a coupling fluid, for example, water. The chamber 4 is closed at an open end by a stretchable membrane 3. A shock wave generator 5 is positioned at a focal point of the focusing chamber 4 and this generator will transmit shock waves to the coupling fluid which surrounds it. The generator operates in accordance with the principles set forth in the above mentioned U.S. Pat. No. 3,942,531, for example, and is connected to a supply unit or power supply 9. The generated shock wave which is created by a spark discharge at the generator first proceeds through the focusing chamber 4 in the coupling fluid and is partially reflected by the inside wall surfaces 6 to proceed to the body of the patient 2 through the elastic membrane 3, as well as via a coupling fluid 10, which is positioned between the skin of the patient 2 and the membrane. The shock wave will be focused at a second focal point 7. The apparatus 20 is positioned on the patient so that the second focal point 7 is situated inside the concrements 8 which is to be disintegrated.

A ring 11 is fastened to the housing 1 to surround the opening of the chamber 4, which is closed by the membrane 3. The ring 11 contains a channel system 12 and is composed, for example, of a microcellular rubber which provides a pliant edge 13 facing the patient 2. The pliant edge 13 of the ring 11 can also be intentionally preshaped to comply with the portion of the body on which the apparatus is to be provided. The channel system 12 comprises two channels 22 and 23 both of which can be used to extract air, which is enclosed in a space 21, which is formed between the membrane 3, the skin of the patient 2 and the ring 11. In addition, the channels 22 can be used for injecting an arbitrary coupling fluid for wetting the skin and the membrane 3. For this purpose, for example, one 22 of the two channels is provided with a fine nozzle 14. The coupling fluid in the focusing chamber 4 can also be supplied or removed through a channel 15 which is a closeable channel and extends to a source of fluid.

In its idle condition, the elastic membrane 3, which is, for example, made of a latex material, is positioned as illustrated to extend in a plane across the mouth of the chamber 4. With the membrane in the position illustrated by the membrane 3, the apparatus 20 is assembled onto the patient in the following procedure:

The channel 15 is closed and the space 21, which is bounded by the membrane 3, the ring 11 and the skin of the patient 2 is first evacuated by applying a vacuum through the channel system 12, such as through the channel 23 thereof. The underpressure or evacuation in the space 21 will cause an opening of the pores in the skin so that the air enclosed in the pores will escape or what air that remains in the pores is also placed under a vacuum pressure.

In this condition, a coupling fluid is injected into the evacuated space through the channel system 12, such as through the channel 22 and the nozzles 14. This fluid will wet the skin 2 of the patient and also the surface of the membrane 3 with the coupling fluid.

Air is continued to be evacuated out of the space through the other channel 23 of the channel system 12 in order to maintain the prevailing vacuum. When an adequately good wetting of the skin has been accomplished, the channels of the channel system 12 are closed and the channel 15 for the focusing chamber 4 is open. Additional coupling fluid enters in through this channel 15 to restore normal pressure in the focusing chamber and cause the membrane 3 to arch outward towards the skin surface to an ever increasing degree. Since the center of the membrane moves furthest from the idle position 3, it will be the first to contact the skin surface moistened with the coupling fluid. The membrane then has a position indicated at 3' with a center portion 25 engaging a thin layer 10 of the wetting fluid on the surface of the skin of the patient 2. With a continued arching of the membrane, it will press against the skin moistened with the coupling fluid and pressing there against to proceed radially from the center 25 and simultaneously expels existing air spaces in a radially outward direction. The pressure building up in the chamber 4 will cause the fluid between the skin and the membrane to be pressed into the pore cavities which were evacuated in the first step. When the membrane is in the final position 3", a large part of the skin surface is covered by the membrane and is only separated therefrom by a thin film of the coupling fluid 10 which prevents a decrease in the coupling caused by natural irregularities of the skin, such as hair, wrinkles and scales. A remaining, slight underpressure additionally sees to a firm, stable seating of the membrane of the apparatus against the skin of the patient 2.

With the assistance of the described apparatus 20, a coupling of the shock waves generated in the chamber 4 into the body of the patient which will be improved over that obtained by the prior art devices. This is due to the fact that no air spaces are enclosed between the skin and the membrane along the coupling surface.

The realization of the apparatus 20 of the invention is not limited to the use of a generator that works with the assistance of a spark discharge. Alternate embodiments can be based on other principles of acoustic generation, for example, by applying a piezo-electric disk or by an electrodynamic sound generator. The use of the other focusing means, such as lenses and/or mirrors, is also possible.

Although various minor modifications may be suggested by those versed in the art, it should be understood that we wish to embody with the scope of the patent granted hereon, all such modifications as reasonably and properly come within the scope of our contribution to the art.

We claim:

1. In an apparatus for acoustic irradiation of a pathological change in a patient, said apparatus including a housing containing a focusing chamber filled with a fluid and closed by a stretchable membrane and a shock wave generator disposed in said chamber to emit shock waves through the fluid of the chamber, the improvements comprising a ring of elastic material being fastened to the housing of the apparatus to surround the stretchable membrane, said ring projecting beyond the membrane while the membrane is in the idle position, said ring having a channel system of at least two separate channels, one of said channels being connected to a evacuation means and the other of said channels being connected to a supply of coupling fluid so that a space defined by the membrane, ring and a skin of the patient engaged by the ring can be evacuated and filled with a coupling fluid.

2. In an apparatus according to claim 1 which further includes said focusing chamber being connected to a closeable channel to enable introducing additional fluid into the chamber to expand the membrane against the skin of the patient.

3. A method of mounting an apparatus for acoustically irradiating a pathological change in a patient, said method comprising providing an apparatus having a housing surrounding a fluid-filled focusing chamber containing a shock wave generator closed by a stretchable membrane, said housing having a ring of elastic material surrounding the membrane, said ring being provided with a channel system having at least two channels and said housing having an additional channel connected to the fluidfilled focusing chamber; positioning the ring to engage the skin of the patient; evacuating a space defined by the skin of the patient, the elastic ring and membrane; then spraying a coupling fluid into the evacuated space; continuing evacuation and spraying until the surface of the membrane facing the skin as well as the skin is thoroughly wetted with the coupling fluid; then stopping the evacuation and introducing additional fluid into the focusing chamber to arch the center of the membrane into contact with the skin; and continuing the introduction of additional fluid to expand the membrane radially from the center outward to engage the skin with a thin layer of coupling fluid therebetween.

* * * * *